United States Patent [19]

Waterson

[11] Patent Number: 5,258,399

[45] Date of Patent: Nov. 2, 1993

[54] SULPHONAMIDE DERIVATIVES

[75] Inventor: David Waterson, Macclesfield, England

[73] Assignees: Imperial Chemical Industries PLC, London, England; ICI Pharma, Cergy Cedex, France

[21] Appl. No.: 995,009

[22] Filed: Dec. 22, 1992

Related U.S. Application Data

[62] Division of Ser. No. 818,911, Jan. 10, 1992.

[30] Foreign Application Priority Data

Jan. 17, 1991 [EP] European Pat. Off. ........ 91400098.9
Jul. 8, 1991 [EP] European Pat. Off. ........ 91401882.5

[51] Int. Cl.$^5$ ............... A61K 31/40; A61K 31/405; C07D 401/00; C07D 209/04
[52] U.S. Cl. ..................... 514/414; 514/415; 514/339; 546/273; 548/490
[58] Field of Search .............. 514/414, 415, 339; 548/490; 546/273

[56] References Cited

U.S. PATENT DOCUMENTS

| | | |
|---|---|---|
| 3,661,917 | 5/1972 | Kaiser et al. . |
| 3,743,737 | 7/1973 | Kaiser et al. . |
| 4,567,184 | 1/1986 | Musser et al. . |
| 4,625,034 | 11/1986 | Neiss et al. . |
| 4,631,287 | 12/1986 | Chakraborty et al. . |
| 4,725,619 | 2/1988 | Chakraborty et al. . |
| 4,728,668 | 3/1988 | Chakraborty et al. . |
| 4,794,188 | 12/1988 | Musser et al. . |
| 4,839,369 | 6/1989 | Youssefyeh et al. . |
| 4,876,346 | 10/1989 | Musser et al. . |
| 4,918,081 | 4/1990 | Huang et al. . |
| 4,920,130 | 4/1990 | Huang et al. . |
| 4,920,131 | 4/1990 | Huang et al. . |
| 4,920,132 | 4/1990 | Huang et al. . |
| 4,920,133 | 4/1990 | Huang et al. . |
| 5,098,930 | 3/1992 | Edwards . |
| 5,098,932 | 3/1992 | Hamon . |
| 5,105,020 | 4/1992 | Girodeau . |

FOREIGN PATENT DOCUMENTS

| | | |
|---|---|---|
| 0110405 | 6/1984 | European Pat. Off. . |
| 0181568 | 5/1986 | European Pat. Off. . |
| 0190722 | 8/1986 | European Pat. Off. . |
| 0200101 | 12/1986 | European Pat. Off. . |
| 0271287 | 6/1988 | European Pat. Off. . |

*Primary Examiner*—Marianne M. Cintins
*Assistant Examiner*—Rebecca Cook
*Attorney, Agent, or Firm*—Cushman, Darby & Cushman

[57] ABSTRACT

The invention concerns sulphonamide derivatives of the formula I

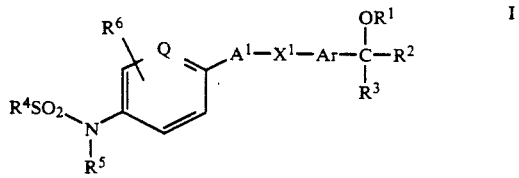

wherein $R^1$ includes (1-4C)alkyl;

$R^2$ and $R^3$ together form $-A^2-X^2-A^3-$ which defines a ring having 5 to 7 ring atoms, wherein $A^2$ and $A^3$ each is (1-3C)alkylene and $X^2$ is oxy, thio, sulphinyl or sulphonyl;

$A^1$ is a direct link to $X^1$ or is (1-3C)alkylene;

$X^1$ is oxy, thio, sulphinyl, sulphonyl or imino;

Ar is optionally substituted phenylene or Ar is pyridylene;

Q is nitrogen or of the formula $CR^7$, wherein $R^7$ includes hydrogen, halogeno, (1-4C)alkyl and (1-4C)alkoxy;

each of $R^4$ and $R^5$ is (1-4C)alkyl, (3-4C)alkenyl, (3-4C)alkynyl or optionally substituted phenyl, benzyl or pyridyl, or $R^5$ may be hydrogen; and $R^6$ has any of the meanings defined for $R^7$;

or a pharmaceutically-acceptable salt thereof;

processes for their manufacture; pharmaceutical compositions containing them and their use as 5-lipoxygenase inhibitors.

6 Claims, No Drawings

SULPHONAMIDE DERIVATIVES

This is a division of application No. 07/818,911, filed Jan. 10, 1992.

This invention concerns novel sulphonamide derivatives and more particularly novel sulphonamide derivatives which are inhibitors of the enzyme 5-lipoxygenase (hereinafter refered to as 5-LO). The invention also concerns processes for the manufacture of said sulphonamide derivatives and novel pharmaceutical compositions containing them. Also included in the invention is the use of said sulphonamide derivatives in the treatment of various inflammatory and/or allergic diseases in which the direct or indirect products of 5-LO catalysed oxidation of arachidonic acid are involved, and the production of new medicaments for such use.

As stated above the sulphonamide derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptide-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G.W. Taylor and S.R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is disclosed in European Patent Application No 0375404 A2 that certain heterocyclic derivatives possess inhibitory properties again 5-LO. Copending European Patent Application No. 90306765.0 (published on Jan. 23, 1991 as European Patent Application No. 0409413) is concerned with diaryl ether heterocycles which also possess inhibitory properties against 5-LO. We have now discovered that certain sulphonamide derivatives which possess some structural features which are similar to those of the compounds disclosed in the above-mentioned applications but which possess other structural features, in particular a sulphonamido substituent, which were not envisaged in those earlier applications, are effective inhibitors of the enzyme 5-LO and thus of leukotriene biosyntheses. Thus such compounds are of value as therapeutic agents in the treatment of, for example allergic conditions, psoriasis, asthma, cardiovasular and cerebrovascular disorders, and/or inflammatory and arthritic conditions, mediated alone or in part by one or more leukotrienes.

According to the invention there is provided a sulphonamide derivative of the formula I (set out hereinafter)
wherein $R^1$ is (1–4C)alkyl, (3–4C)alkenyl or (3–4C)alkynyl; and wherein $R^2$ and $R^3$ together form a group of the formula $—A^2—X^2—A^3—$ which, together with the carbon atom to which $A^2$ and $A^3$ are attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three substituents, which may be the same or different, selected from hydroxy, (1–4C)alkyl and (1–4C)alkoxy;

or wherein $R^1$ and $R^2$ together form a group of the formula $—A^2—X^2—A^3—$ which together with the oxygen atom to which $A^2$ is attached and with the carbon atom to which $A^3$ is attached, defines a ring having 5 to 7 ring atoms, wherein $A^2$ and $A^3$, which may be the same or different, each is (1–3C)alkylene and $X^2$ is oxy, thio, sulphinyl or sulphonyl and which ring may bear one, two or three (1–4C)alkyl substituents, and wherein $R^3$ is (1–4C)alkyl, (2–4C)alkenyl or (2–4C)alkynyl; wherein $A^1$ is a direct link to $X^1$ or is (1–3C)alkylene;

wherein $X^1$ is oxy, thio, sulphinyl, sulphonyl or imino;
wherein Ar is phenylene which may optionally bear one or two substituents selected from halogeno, hydroxy, amino, nitro, cyano, carbamoyl, ureido, (1–4C)alkyl, (1–4C)alkoxy, (1–4C)alkylamino, di-[(1–4C)alkyl]amino, fluoro-(1–4C)alkyl and (2–4C)alkanoylamino; or Ar is pyridylene;
and wherein Q is nitrogen or of the formula $CR^7$, wherein $R^7$ is hydrogen, halogeno, (1–4C)alkyl, (1–4C)alkoxy, hydroxy, amino, nitro, cyano, carbamoyl, ureido, (1–4C)alkylamino, di-[(1–4C)alkyl]amino, fluoro-(1–4C)alkyl, (2–4C)alkanoylamino or (2–4C)alkenyl;

wherein $R^4$ is (1–4C)alkyl, (3–4C)alkenyl or (3–4C)alkynyl or $R^4$ is phenyl, benzyl or pyridyl each of which may optionally bear one or two substituents selected from halogeno, (1–4C)alkoxy, (1–4C)alkyl, hydroxy, cyano, nitro, amino, trifluoromethyl, carbamoyl, ureido, (1–4C)alkylamino, di-[(1–4C)alkyl]amino and (2–4C)alkanoylamino;

wherein $R^5$ is hydrogen, (1–4C)alkyl, (3–4C)alkenyl or (3–4C)alkynyl, or $R^5$ is phenyl, benzyl, or pyridyl each of which may optionally bear one or two substituents selected from halogeno, (1–4C)alkoxy, (1–4C)alkyl, hydroxy, cyano, nitro, amino, trifluoromethyl, carbamoyl, ureido, (1–4C)alkylamino, di-[(1–4C)alkyl]amino and (2–4C)alkanoylamino;

wherein $R^6$ is hydrogen, halogeno, (1–4C)alkyl, (1–4C)alkoxy, hydroxy, amino, nitro, cyano, carbamoyl, ureido, (1–4C)alkylamino, di-[(1–4C)-alkyl]amino, fluoro-(1–4C)alkyl or (2–4C)alkanoylamino; or $R^5$ and $R^6$ may be joined to form (2–4C)alkylene or (2–4C)alkenylene either of which may optionally bear one or two substituents selected from (1–4C)alkyl and halogens;

or a pharmaceutically-acceptable salt thereof.

According to a further aspect of the invention there is provided a sulphonamide derivative of the formula I as defined hereinbefore wherein $R^4$ may be phenyl, benzyl, naphthyl, pyridyl or quinolyl each of which may optionally bear one or two substituents selected from halogeno, (1–4C)alkoxy, (1–4C)alkyl, hydroxy, cyano, nitro, amino, trifluoromethyl, carbamoyl, ureido, (1–4C)alkylamino, di-[(1–4C)alkyl]amino, (2–4C)alkanoylamino and (1–4C)alkoxycarbonyl; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilised within the formulae drawings.

It is further to be understood that, insofar as certain of the compounds of formula I defined above may exist in optically active or racemic forms by virtue of one or more substituents containing an asymmetric carbon atom, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for $R^1$ when it is (1–4C)alkyl is, for example, methyl, ethyl, propyl or butyl; when it is (3–4C)alkenyl is, for example, allyl, 2-butenyl or 3-butenyl; and when it is (3–4C)alkynyl is, for example, 2-propynyl or 2-butynyl.

When $R^2$ and $R^3$ together form a group of the formula —$A^2$—$X^2$—$A^3$—which, together with the carbon atom to which $A^2$ and $A^3$ are attached, defines a ring having 5 to 7 ring atoms then a suitable value for $A^2$ and $A^3$, which may be the same or different, when each is (1–3C)alkylene is, for example, methylene, ethylene or trimethylene. Suitable values for the substituents which may be present on said 5-to 7-membered ring include for example:-

| | |
|---|---|
| for (1–4C)alkyl: | methyl, ethyl, propyl, isopropyl, butyl and isobutyl; |
| for (1–4C)alkoxy: | methoxy, ethoxy, propoxy, isopropoxy and butoxy. |

When $R^1$ and $R^2$ together form a group of the formula —$A^2$—$X^2$—$A^3$—which together with the oxygen atom to which $A^2$ is attached and with the carbon atom to which $A^3$ is attached, defines a ring having 5 to 7 ring atoms then a suitable value for $A^2$ and $A^3$, which may be the same or different, when each is (1–3C)alkylene is, for example, methylene, ethylene or trimethylene. Suitable values for the (1–4C)alkyl substituents which may be present on said 5- to 7-membered ring include, for example, methyl, ethyl, propyl, isopropyl and butyl.

A suitable value for $R^3$ when it is (1–4C)alkyl is, for example, methyl, ethyl, propyl or butyl; when it is (2–4C)alkenyl is, for example, vinyl, allyl, 2-butenyl or 3-butenyl; and when it is (2–4C)alkynyl is, for example, ethynyl, 2-propynyl or 2-butynyl.

A suitable value for $A^1$ when it is (1–3C)alkylene is, for example, methylene, ethylene or trimethylene.

A suitable value for Ar when it is phenylene is, for example, 1,3-phenylene or 1,4-phenylene.

A suitable value for Ar when it is pyridylene is, for example, 3,5- or 2,6-pyridylene.

A suitable value for a halogeno substituent which may be present on Ar is, for example, fluoro, chloro, bromo or iodo.

A suitable value for a (2–4C)alkanoylamino substituent which may be present on Ar is, for example, acetamido, propionamido or butyramido.

A suitable value for a (1–4C)alkyl substituent which may be present on Ar is, for example, methyl, ethyl, propyl, isopropyl, butyl, isobutyl, sec-butyl or tert-butyl.

A suitable value for a (1–4C)alkoxy substituent which may be present on Ar is, for example, methoxy, ethoxy, propoxy, isopropoxy or butoxy.

A suitable value for a (1–4C)alkylamino substituent which may be present on Ar is, for example, methylamino, ethylamino, propylamino, isopropylamino, butylamino, isobutylamino, sec-butylamino or tert-butylamino.

A suitable value for a di-[(1–4C)alkyl]amino substituent which may be present on Ar is, for example, dimethylamino, diethylamino, dipropylamino, dibutylamino or ethylmethylamino.

A suitable value for a fluoro-(1–4C)alkyl substituent which may be present on Ar is, for example, fluoromethyl, fluoroethyl, fluoropropyl, fluoroisopropyl, fluorobutyl, difluoromethyl or trifluoroethyl.

Suitable values for $R^7$ include, for example:

| | |
|---|---|
| for halogeno: | fluoro, chloro, bromo and iodo; |
| for (1–4C)alkyl: | methyl, ethyl, propyl, isopropyl, butyl, isobutyl, sec-butyl and tert-butyl; |
| for (1–4C)alkoxy: | methoxy, ethoxy, propoxy, isopropoxy and butoxy; |
| for (1–4C)alkylamino: | methylamino, ethylamino, propylamino, isopropylamino, butylamino, sec-butylamino and tert-butylamino; |
| for di-[(1–4C)alkyl] amino: | dimethylamino, diethylamino, dimethylamino, diethylamino, dipropylamino, ethylmethylamino and dibutylamino; |
| for fluoro-(1–4C)alkyl: | fluoromethyl, fluoroethyl, difluoromethyl, trifluoromethyl, fluoropropyl, fluorobutyl and fluoroisopropyl; |
| for (2–4C)alkanoyl- amino: | acetamido, propionamido and butyramido; |
| for (2–4C)alkenyl: | vinyl, allyl, 2-butenyl and 3-butenyl. |

A suitable value for $R^4$ when is it (1–4C)alkyl is, for example, methyl, ethyl, propyl, isopropyl, butyl, sec-butyl or tert-butyl.

A suitable value for $R^4$ when it is (3–4C)alkenyl is, for example, allyl, 2-butenyl or 3-butenyl.

A suitable value for $R^4$ when it is (3–4C)alkynyl is, for example, 2-propynyl or 2-butynyl.

A suitable value for $R^4$ or $R^5$ when it is pyridyl is, for example, 2-pyridyl, 3-pyridyl or 4-pyridyl.

A suitable value for $R^4$ when it is naphthyl is, for example, 1-naphthyl or 2-naphthyl, especially 1-naphthyl.

A suitable value for $R^4$ when it is quinolyl is, for example, 2-, 3-, 4-, 5-, 6-, 7- or 8-quinolyl, especially 8-quinolyl.

A suitable value for $R^5$ when is it (1–4C)alkyl is, for example, methyl, ethyl, propyl, isopropyl, butyl, sec-butyl or tert-butyl.

A suitable value for $R^5$ when it is (3–4C)alkenyl is, for example, allyl, 2-butenyl or 3-butenyl.

A suitable value for $R^5$ when it is (3–4C)alkynyl is, for example, 2-propynyl or 2-butynyl.

- Suitable values for substituents which may be present on $R^4$ or $R^5$ when each is phenyl, benzyl, naphthyl, pyridyl or quinolyl include, for example:

| | |
|---|---|
| for halogeno: | fluoro, chloro, bromo and iodo; |
| for (1-4C)alkoxy: | methoxy, ethoxy, propoxy, isopropoxy and butoxy; |
| for (1-4C)alkyl: | methyl, ethyl, propyl, isopropyl, sec-butyl and tert-butyl; |
| for (1-4C)alkylamino: | methylamino, ethylamino, propylamino, isopropylamino, butylamino, sec-butylamino and tert-butylamino; |
| for di-[(1-4C)alkyl]amino: | dimethylamino, diethylamino, dipropylamino, dibutylamino and ethylmethylamino; |
| for (2-4C)alkanoylamino: | acetamido, propionamido and butyramido; |
| for (1-4C)alkoxycarbonyl: | methoxycarbonyl, ethoxycarbonyl propoxycarbonyl and tert-butoxycarbonyl. |

Suitable values for $R^6$ include, for example:-

| | |
|---|---|
| for halogeno: | fluoro, chloro, bromo and iodo; |
| for (1-4C)alkyl: | methyl, ethyl, propyl, isopropyl, butyl, isobutyl, sec-butyl and tert-butyl; |
| for (1-4C)alkoxy: | methoxy, ethoxy, propoxy, isopropoxy and butoxy; |
| for (1-4C)alkylamino: | methylamino, ethylamino, propylamino, isopropylamino, butylamino, sec-butylamino and tert-butylamino; |
| for di[(1-4C)alkyl]amino: | dimethylamino, diethylamino, dipropylamino, ethylmethylamino and dibutylamino; |
| for fluoro-(1-4C)alkyl: | fluoromethyl, fluoroethyl, difluoromethyl, trifluoromethyl, fluoropropyl, fluorobutyl and fluoroisopropyl; |
| for (2-4C)alkanoylamino: | acetamido, propionamido and butyramido. |

A suitable value for $R^5$ and $R^6$ when they are joined to form (2–4C)alkylene is, for example, ethylene or trimethylene. Conveniently $R^6$ is located at the position ortho to the $R^4SO_2NR^5$ group.

A suitable value for $R^5$ and $R^6$ when they are joined to form (2–4C)alkenylene is, for example, vinylene, prop-1-en-1,3-diyl or prop-2-en-1,3-diyl. Conveniently $R^6$ is located at the position ortho to the $R^4SO_2NR^5$ group.

Suitable values for the substituents which may be present on the (2–4C)alkylene or (2–4C)alkenylene group when $R^5$ and $R^6$ are joined include, for example:-

| | |
|---|---|
| for halogeno: | fluoro, chloro, bromo and iodo; |
| for (1-4C)alkyl: | methyl, ethyl and propyl. |

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention include, for example, sulphonamide derivatives of the formula I wherein:-

(a) $R^1$ is methyl, ethyl, allyl or 2-propynyl; and Q, $R^2$, $R^3$, $A^1$, $X^1$, Ar, $R^4$, $R^5$ and $R^6$ have any of the meanings defined hereinbefore;

(b) $R^2$ and $R^3$ together form a group of the formula $-A^2-X^2-A^3-$ which, together with the carbon atom to which $A^2$ and $A^3$ are attached, defines a ring having 5 to 7 ring atoms, wherein $A^2$ and $A^3$, which may be the same or different, each is methylene, ethylene or trimethylene and $X^2$ is oxy, and which ring may bear one or two substituents selected from hydroxy, methyl, ethyl, propyl, methoxy and ethoxy; and Q, $R^1$, $A^1$, $X^1$, Ar, $R^4$, $R^5$ and $R^6$ have any of the meanings defined hereinbefore:

(c) $R^1$ and $R^2$ together form a group of the formula $-A^2-X^2-A^3-$which, together with the oxygen atom to which $A^2$ is attached and with the carbon atom to which $A^3$ is attached, defines a ring having 5 to 7 ring atoms, wherein $A^2$ and $A^3$, which may be the same or different, each is methylene or ethylene and $X^2$ is oxy, and which ring may bear one, two or three substituents selected from methyl, ethyl and propyl, and $R^3$ is methyl or ethyl; and Q, $A^1$, $X^1$, Ar, $R^4$, $R^5$ and $R^6$ have any of the meanings defined hereinbefore;

(d) $A^1$ is a direct link to $X^1$, and $X^1$ is oxy, thio, sulphinyl or sulphonyl; and Q, $R^1$, $R^2$, $R^3$, Ar, $R^4$, $R^5$ and $R^6$ have any of the meanings defined hereinbefore;

(e) $A^1$ is methylene and $X^1$ is oxy, thio, sulphinyl or sulphonyl; and Q, $R^1$, $R^2$, $R^3$, Ar, $R^4$, $R^5$ and $R^6$ have any of the meanings defined hereinbefore;

(f) Ar is 1,3-phenylene or 1,4-phenylene which may optionally bear one or two substituents selected from fluoro, chloro, hydroxy, amino, nitro, ureido, methyl, methoxy, methylamino, dimethylamino, trifluoromethyl and acetamido; and Q, $A^1$, $X^1$, $R^1$, $R^2$, $R^3$, $R^4$, $R^5$ and $R^6$ have any of the meanings defined hereinbefore;

(g) Ar is 3,5-pyridylene; and Q, $A^1$, $X^1$, $R^1$, $R^2$, $R^3$, $R^4$, $R^5$ and $R^6$ have any of the meanings defined hereinbefore;

(h) Q is nitrogen or a group of the formula $CR^7$, wherein $R^7$ is hydrogen, methyl, ethyl, propyl, methoxy, ethoxy, propoxy, fluoro, chloro or hydroxy; and $R^1$, $R^2$, $R^3$, $A^1$, $X^1$, Ar, $R^4$, $R^5$ and $R^6$ have any of the meanings defined hereinbefore;

(i) $R^4$ is methyl, ethyl, propyl, phenyl, benzyl or 3-pyridyl each of which may bear one or two substituents selected from fluoro, chloro, methoxy, ethoxy, methyl, ethyl or hydroxy; and Q, $R^1$, $R^2$, $R^3$, $A^1$, $X^1$, Ar, $R^5$ and $R^6$ have any of the meanings defined hereinbefore;

(j) $R^4$ is methyl, ethyl, propyl, phenyl, benzyl, 1-naphthyl, 3-pyridyl or 8-quinolyl each of which may bear one or two substituents selected from fluoro, chloro, methoxy, ethoxy, methyl, ethyl, hydroxy, methoxycarbonyl or ethoxycarbonyl; and Q, $R^1$, $R^2$, $R^3$, $A^1$, $X^1$, Ar, $R^5$ and $R^6$ have any of the meanings defined hereinbefore;

(k) $R^5$ is hydrogen, methyl, ethyl, propyl, allyl, phenyl or benzyl each of which may bear one or two substituents selected from fluoro, chloro, methoxy, ethoxy, methyl, ethyl or hydroxy; and Q, $R^1$, $R^2$, $R^3$, $A^1$, $X^1$, Ar, $R^4$ and $R^6$ have any of the meanings defined hereinbefore;

(l) $R^6$ is hydrogen, methyl, ethyl, propyl, methoxy, ethoxy, fluoro, chloro or hydroxy; and Q, $R^1$, $R^2$, $R^3$, $A^1$, $X^1$, Ar, $R^4$ and $R^5$ have any of the meanings defined hereinbefore;

(m) $R^5$ and $R^6$ are joined together to form ethylene, trimethylene or vinylene which may bear one or two substituents selected from methyl, ethyl and propyl; and Q, $R^1$, $R^2$, $R^3$, $A^1$, $X^1$, Ar and $R^4$ have any of the meanings defined hereinbefore;

(n) Q is nitrogen; and $R^1$, $R^2$, $R^3$, $A^1$, $X^1$, Ar, $R^4$, $R^5$ and $R^6$ have any of the meanings defined hereinbefore;

(o) Q is a group of the formula $CR^7$, wherein $R^7$ is hydrogen, fluoro, chloro, methyl, ethyl or methoxy; and $R^1$, $R^2$, $R^3$, $A^1$, $X^1$, Ar, $R^4$, $R^5$ and $R^6$ have any of the meanings defined hereinbefore;

(p) $R^4$ is methyl, ethyl or propyl or $R^4$ is phenyl which may bear one or two substituents selected from fluoro, chloro, methyl or methoxy; and Q, $R^1$, $R^2$, $R^3$, $A^1$, $X^1$ Ar, $R^5$ and $R^6$ have any of the meanings defined hereinbefore;

(q) $R^5$ is hydrogen, methyl, ethyl, propyl or allyl or $R^5$ is phenyl or benzyl which may bear one or two substituents selected from fluoro, chloro, methyl or methoxy; and Q, $R^1$, $R^2$, $R^3$, $A^1$, $X^1$, Ar, $R^4$ and $R^6$ have any of the meanings defined hereinbefore;

(r) $R^5$ is hydrogen; and Q, $R^1$, $R^2$, $R^3$, $A^1$, $X^1$, Ar, $R^4$ and $R^6$ have any of the meanings defined hereinbefore; or (s) $R^6$ is located at the position ortho to the $R^4SO_2NR^5$ group and $R^5$ and $R^6$ are joined together to form ethylene or trimethylene; and Q, $R^1$, $R^2$, $R^3$, $A^1$, $X^1$, Ar and $R^4$ have any of the meanings defined hereinbefore;

or a pharmaceutically-acceptable salt thereof.

A preferred compound of the invention comprises a sulphonamide derivative of the formula I wherein $R^1$ is methyl, ethyl, allyl or 2-propynyl;

$R^2$ and $R^3$ together form a group of the formula —$A^2$—$X^2$—$A^3$—which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl, ethyl, propyl, methoxy and ethoxy;

or $R^1$ and $R^2$ together form a group of the formula —$A^2$—$X^2$—$A^3$—which, together with the oxygen atom to which $A^2$ is attached and with the carbon atom to which $A^3$ is attached, defines a ring having 5 or 6 ring atoms, wherein $A^2$ is methylene, $A^3$ is methylene or ethylene, and $X^2$ is oxy, and which ring may bear one, two or three substituents selected from methyl, ethyl and propyl, and $R^3$ is methyl or ethyl;

$A^1$ is a direct link to $X^1$ is methylene;

$X^1$ is oxy, thio, sulphinyl or sulphonyl;

Ar is 1,3-phenylene or 1,4-phenylene which may optionally bear one or two substituents selected from fluoro, chloro, hydroxy, amino, nitro, ureido, methoxy, dimethylamino, trifluoromethyl and acetamido; or Ar is 3,5-pyridylene;

Q is nitrogen or of the formula $CR^7$ wherein $R^7$ is hydrogen, fluoro, chloro, methyl, ethyl, propyl, methoxy, ethoxy, hydroxy, amino, methylamino, dimethylamino or trifluoromethyl;

$R^4$ is methyl, ethyl, propyl, allyl, phenyl, benzyl, 3-pyridyl, 2-hydroxyethyl, 3-hydroxypropyl, 2-chloroethyl or 3-chloropropyl;

$R^5$ is hydrogen, methyl, ethyl, propyl, phenyl, benzyl, allyl, 3-pyridyl, 2-hydroxyethyl, 3-hydroxypropyl, 2-chloroethyl, 3-chloropropyl or 2-methoxyethyl; and $R^6$ is hydrogen, fluoro, chloro, methyl, ethyl, propyl, methoxy, ethoxy, hydroxy, amino, methylamino, dimethylamino or trifluoromethyl; or $R^5$ and $R^6$ may be joined to form ethylene, trimethylene or vinylene; or a pharmaceutically-acceptable salt thereof.

A further preferred compound of the invention comprises a sulphonamide derivative of the formula I wherein $R^1$ is methyl;

$R^2$ and $R^3$ together form a group of the formula —$A^2$—$X^2$—$A^3$—which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;

$A^1$ is a direct link to $X^1$, or is methylene;

$X^1$ is thio or oxy;

Ar is 1,3-phenylene which may optionally bear a fluoro substituent;

Q is nitrogen or of the formula $CR^7$ wherein $R^7$ is hydrogen, methyl or chloro;

$R^4$ is methyl, ethyl or phenyl;

$R^5$ is hydrogen, methyl, ethyl, allyl or benzyl; and $R^6$ is hydrogen, methyl or chloro; or $R^5$ and $R^6$ may be joined to form ethylene or trimethylene; or a pharmaceutically-acceptable salt thereof.

A further preferred compound of the invention comprises a sulphonamide derivative of the formula I wherein $R^1$ is methyl;

$R^2$ and $R^3$ together form a group of the formula —$A^2$—$X^2$—$A^3$—which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;

$A^1$ is a direct link to $X^1$, or is methylene;

$X^1$ is thio or oxy;

Ar is 1,3-phenylene which may optionally bear a fluoro substituent;

Q is of the formula $CR^7$ wherein $R^7$ is hydrogen, methyl or chloro;

$R^4$ is methyl, ethyl or phenyl;

$R^5$ is hydrogen;

$R^6$ is hydrogen, methyl, fluoro or chloro;

or a pharmaceutically-acceptable salt thereof.

A further preferred compound of the invention comprises a sulphonamide derivative of the formula I, wherein $R^1$ is methyl; $R^2$ and $R^3$ together form a group of the formula —$A^2$—$X^2$—$A^3$—which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl substituent alpha to $X^2$;

$A^1$ is a direct link to $X^1$;

$X^1$ is thio;

Ar is 1,3-phenylene;

Q is of the formula $CR^7$ wherein $R^7$ is hydrogen;

$R^4$ is methyl;

$R^5$ is methyl of ethyl; and $R^6$ is hydrogen or chloro;

or a pharmaceutically-acceptable salt thereof.

A further preferred compound of the invention comprises a sulphonamide derivative of the formula I wherein $R^1$ is methyl;

$R^2$ and $R^3$ together form a group of the formula —$A^2$—$X^2$—$A^3$—which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;

$A^1$ is a direct link to $X^1$;

$X^1$ is thio;

Ar is 1,3-phenylene which may optionally bear a fluoro substituent;

Q is of the formula $CR^7$ wherein $R^7$ is hydrogen or chloro;

$R^4$ is methyl, ethyl, phenyl, 2-methoxycarbonylphenyl or 8-quinolyl;

$R^5$ is hydrogen;

$R^6$ is hydrogen, fluoro or chloro;

or a pharmaceutically-acceptable salt thereof.

A further preferred compound of the invention comprises a sulphonamide derivative of the formula I, wherein $R^1$ is methyl;

$R^2$ and $R^3$ together form a group of the formula —$A^2$—$X^2$—$A^3$—which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl substituent alpha to $X^2$;

$A^1$ is a direct link to $X^1$;

$X^1$ is thio;

Ar is 1,3-phenylene or 5-fluoro-1,3-phenylene;

Q is of the formula $CR^7$ wherein $R^7$ is hydrogen or chloro;

$R^4$ is methyl;

$R^5$ is hydrogen; and $R^6$ is hydrogen, fluoro or chloro;

or a pharmaceutically-acceptable salt thereof.

A specific especially preferred compound of the invention is, for example, the following sulphonamide derivative of the formula I, or a pharmaceutically-acceptable salt thereof:

N-{4-[3-(4-methoxytetrahydropyran-4-yl)phenylthio]-phenyl}-N-methyl-methanesulphonamide, N-{3-chloro-4-[3-(4-methoxytetrahydropyran-4-yl)phenylthio]phenyl}-N-methylmethanesulphonamide, N-{4-[3-(4-methoxytetrahydropyran-4-yl)phenylthio]-phenyl}-N-ethyl-methanesulphonamide or N-{4-[3-(4-methoxytetrahydropyran-4-yl)phenylthiol-phenyl}-N-methyl-ethanesulphonamide.

A further specific especially preferred compound of the invention is, for example, the following sulphonamide derivative of the formula I, or a pharmaceuticaly-acceptable salt thereof:-

N-{2-chloro-4-[3-(4-methoxytetrahydropyran-4-yl)phenylthiolphenyl}-methanesulphonamide, N-{2-chloro-4-[4-[5-fluoro-3-(4-methoxytetrahydropyran-4-yl)-phenylthio]phenyl}methanesulphonamide, N-{3-chloro-4-[5-fluoro-3-(4-methoxytetrahydropyran-4-yl)-phenylthio]phenyl}methansulphonamide or N-{2-fluoro-4-[5-fluoro-3-(4-methoxytetrahydropyran-4-yl)-phenylthio]phenyl}methanesulphonamide.

A compound of the invention comprising a sulphonamide derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated $R^1$, $R^2$, $R^3$, $A^1$, $X^1$, Ar, Q, $R^4$, $R^5$, $R^6$ and $R^7$ have any of the meanings defined hereinbefore.

(a) The coupling, conveniently in the presence of a suitable base, of a compound of the formula II with a compound of the formula III, wherein Z is a displaceable group; provided that, when there is an amino, alkylamino or hydroxy group in Ar, $R^2$, $R^3$, $R^4$, $R^5$, $R^6$ or $R^7$, any amino, alkylamino or hydroxy group may be protected by a conventional protecting group or alternatively any such group need not be protected, whereafter any undesired protecting group in Ar, $R^2$, $R^3$, $R^4$, $R^5$, $R^6$ and $R^7$ is removed by conventional means.

A suitable displaceable group Z is, for example, a halogeno or sulphonyloxy group, for example a chloro, bromo, iodo, methanesulphonyloxy or toluene-4-sulphonyloxy group.

A suitable base for the coupling reaction is, for example, an alkali or alkaline earth metal carbonate, (1–4C-)alkoxide, hydroxide or hydride, for example sodium carbonate, potassium carbonate, sodium ethoxide, potassium butoxide, sodium hydroxide, potassium hydroxide, sodium hydride or potassium hydride. The coupling reaction is conveniently performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 190° C., conveniently at or near 140° C.

Conveniently the reaction may be performed in the presence of a suitable catalyst, for example a metallic catalyst, for example palladium(O) or copper(I) such as tetrakis(triphenylphosphine)-palladium, cuprous chloride or cuprous bromide.

A suitable protecting group for an amino or alkylamino group is, for example, an acyl group for example a (2-4C)alkanoyl group (especially acetyl), a (1-4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example by hydrogenation over a catalyst such as palladium-on-charcoal.

The starting materials of the formula II and of the formula III may be obtained by standard procedures of organic chemistry. The preparation of such starting materials is described within the accompanying non-limiting Examples which are provided for the purpose of illustration only. Alternatively necessary starting materials of the formula III are obtainable by analogous procedures to those illustrated in accompanying Scheme I (set out hereinafter) or by modifications thereto which are within the ordinary skill of an organic chemist.

A suitable protecting group $R^8$, as employed in Scheme I, is any one of the many such groups known in the art and includes any appropriate protecting group as defined hereinbefore. Examples of such groups are given in Scheme I. The conditions for the introduction and removal of such protecting groups are described in standard textbooks or organic chemistry such as, for example, "Protective Groups in Organic Synthesis" by T W Green (J Wiley and Sons, 1981).

(b) The coupling, conveniently in the presence of a suitable base as defined hereinbefore, of a compound of the formula IV with a compound of the formula V wherein Z is a displaceable group as defined hereinbefore; provided that, when there is an amino, alkylamino or hydroxy group in Ar, $R^2$, $R^3$, $R^4$, $R^5$, $R^6$ or $R^7$ any amino, alkylamino or hydroxy group may be protected by a conventional protecting group as defined hereinbefore or alternatively any such group need not be protected, whereafter any undesired protecting group in Ar, $R^2$, $R^3$, $R^4$ $R^5$, $R^6$ or $R^7$ is removed by conventional means.

The coupling reaction is conveniently performed in a suitable inert solvent as defined hereinbefore and at a temperature in the range, for example, 10° to 190° C., conveniently at or near 140° C. The reaction may conveniently be performed in the presence of a suitable catalyst as defined hereinbefore.

Conveniently intermediates of the formula V wherein Z, Ar, $R^1$, $R^2$ and $R^3$ have the meanings defined hereinbefore, may be obtained by way of compounds of the formula Z-Ar-Y, wherein Z and Ar have the meanings defined hereinbefore and Y is, for example, a halogeno, formyl, alkanoyl, nitrile or alkoxycarbonyl group, as illustrated in accompanying Scheme II (set out hereinafter).

It will also be appreciated that the intermediate of the formula V may conveniently be obtained from the compound of the formula Z-Ar-Y, as defined hereinbefore, by reversing the order of introduction of the groups $R^2$ and $R^3$ which is used in Scheme II.

(c) The alkylation, conveniently in the presence of a suitable base as defined hereinbefore, of a compound of the formula VI with a compound of the formula $R^1$-Z, wherein $R^1$ and Z have the meanings defined hereinbefore; provided that, when there is an amino, alkylamino or hydroxy group in Ar, $R^2$, $R^3$, $R^4$, $R^5$, $R^6$ or $R^7$ any amino, alkylamino or hydroxy group may be protected by a conventional protecting group or alternatively any such group need not be protected, whereafter any undesired protecting group in Ar, $R^2$, $R^3$, $R^4$, $R^5$, $R^6$ and $R^7$ is removed by conventional means.

The tertiary alcohol starting material of the formula VI may be obtained by standard procedures of organic chemistry. Conveniently, and as illustrated in accompanying Scheme III (set out hereinafter), intermediates of the formula VIII wherein $A^1$, $X^1$, Ar, Q, $R^4$, $R^5$ and $R^6$ have the meanings defined hereinbefore and Y is, for example, a formyl, nitrile or alkoxycarbonyl group may be utilised in the preparation of the tertiary alcohol starting material of the formula VI.

(d) The sulphonamidification, conveniently in the presence of a Lewis base such as an organic amine, for example triethylamine, pyridine, 4-dimethylaminopyridine, morpholine and piperidine, of a compound of the formula VII with a compound of the formula $R^4SO_2Z$, wherein Z is a displaceable group such as halogeno for example chloro, bromo or iodo; provided that when there is an amino, alkylamino or hydroxy group in Ar, $R^2$, $R^3$, $R^5$, $R^6$ or $R^7$, any amino, alkylamino or hydroxy group is protected by a conventional protecting group as defined hereinbefore, whereafter any undesired protecting group in Ar, $R^2$, $R^3$, $R^5$, $R^6$ or $R^7$ is removed by conventional means.

The reaction is conveniently performed in a suitable organic solvent, for example dichloromethane, N,N-dimethylformamide, N,N-dimethylacetamide, dimethylsulphoxide, acetone, 1,2-dimethoxyethane, N-methylpyrrolidin-2-one or tetrahydrofuran and at a temperature in the range of −40° C. to 80° C. conveniently in the range 0°–25° C.

The starting material of the formula VII may be obtained by standard procedures of organic chemistry such as by analogous procedures to those described hereinbefore in process variants (a) to (c) above or by modifications thereto which are within the skill of an organic chemist.

(e) For the production of those compounds of the formula I wherein $X^1$ is a sulphinyl or sulphonyl group, or wherein $R^2$ and $R^3$ together form a group of the formula $—A^2—X^2—A^3—$ and $X^2$ is a sulphinyl or sulphonyl group, the oxidation of a compound of the formula I wherein $X^1$ is a thio group, or wherein $R^2$ and $R^3$ together form a group of the formula $—A^2—X^2—A^3—$ and $X^2$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae IV and VI and these are provided as a further feature of the invention.

As stated previously, the novel compounds of the formula I are inhibitors of the enzyme 5-LO. The effects of this inhibition may be demonstrated using one or more of the standard procedures set out below:- a) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (*Prostaglandins Leukotrienes Med.*, 1986, 22, 57; *Prostaglandins*, 1984, 28, 666; *Brit. J. Pharmacol.*, 1985, 84, 34P) which involve the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2$($TxB_2$) described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

c) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)-c):-

Test a): $IC_{50}$ ($LTB_4$) in the range, for example, 1.10–40 μM
$IC_{50}$ ($TxB_2$) in the range, for example, 40–200 μM;
Test b): oral $ED_{50}$($LTB_4$) in the range, for example, 1–100 mg/kg;
Test c): oral $ED_{50}$($LTB_4$) in the range, for example, 0.5–50 mg/kg.

No overt toxicity or other untoward effects are present in tests b) and/or c) when compounds of the formula I are administered at several multiples of their minimum inhibitory dose or concentration.

Thus, by way of example, the compound N-{3-chloro-4-[3-(4-methoxytetrahydropyran-4-yl) phenylthio]phenyl}-N-methylmethane-sulphonamide has an $IC_{50}$ of 0.09 μM against $LTB_4$ in test a), and an oral $ED_{50}$ of 1 mg/kg versus $LTB_4$ in test c); and the compound N-{2-chloro-4-[3-(4-methoxytetrahydropyran-4-yl)phenylthio]phenyl}-methanesulphonamide has an $IC_{50}$ of 1 μM against $LTB_4$ in test a), and an oral $ED_{50}$ of 1.5 mg/kg versus $LTB_4$ in test c). In general those compounds of the formula I which are particularly preferred have an $IC_{50}$ of <1 μM against $LTB_4$ in test a), and an oral $ED_{50}$ of <100 mg/kg against $LTB_4$ in tests b) and/or c).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a sulphonamide derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a sulphonamide derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a sulphonamide derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a sulphonamide derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°-25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, W. Germany;

(iv) yields are given for illustration only and are not necessarily the maximum attainable;

(v) the structures of the end-products of the formula I were confirmed by NMR and mass spectral techniques; unless otherwise stated, $CDCl_3$ solutions of the end-products of the formula I were used for the determination of the NMR spectral data, chemical shift values were measured on the delta scale;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after crystallisation from a conventional organic solvent such as ethanol, reethanol, acetone, ether or hexane, alone or in admixture; and (viii) the following abbreviations have been used:

| THF | tetrahydrofuran; |
| DMF | N,N-dimethylformamide. |

EXAMPLE 1

A solution of -N-(4-bromomethylphenyl)-N-methylmethane-sulphonamide (0.36 g), 4-(5-fluoro-3-hydroxyphenyl)-4-methoxytetra-hydropyran (0.27 g) and potassium carbonate (0.36 g) in DMF was stirred at ambient temperature for 18 hours. The mixture was then partitioned between ethyl acetate (75 ml) and water (50 ml) and the organic phase washed with brine (50 ml) and dried (MgSO$_4$). The solvent was evaporated and the product purified by column chromatography. Thus was obtained N-{4-[5-fluoro-3-(4-methoxytetrahydropyran -4-yl)phenoxymethyl]phenyl}-N-methylmethanesulphonamide (0.23 g, 47%), m.p. 128°–132° C. (recrystallised from ethyl acetate/hexane). NMR Spectrum 1.82–2.05 (4H, m), 2.85 (3H, s), 2.98 (3H, s), 3.75–3.91 (4H, m), 5.04 (2H, 2), 6.60 (1H, m), 6.73 (1H, m), 6.80 (1H, m), 7.38–7.50 (4H, m).

The 4-(5-fluoro-3-hydroxyphenyl)-4-methoxytetrahydropyran used as starting material was prepared as described in European Patent Application No 0385662 (example 2 therein).

The N-(4-bromomethylphenyl)-N-methylmethanesulphonamide used as starting material was obtained as follows:

A solution of p-methyl-N-methylaniline (5.00 g) and triethylamine (5.05 g) in dichloromethane (140 ml) was cooled to 0° C. and methanesulphonyl chloride (4.73 g) was added dropwise. The reaction mixture was stirred at ambient temperature for 2 hours and quenched with water (100 ml). The organic phase was washed with 2N aqueous hydrochloric acid solution (75 ml) and 2N aqueous sodium hydroxide solution (75 ml), dried (MGSO ) and the solvent removed by evaporation. Thus was obtained N-methyl-(4-tolyl)methanesulphonamide (5.3 g, 65%), m.p. 49°–52° C.

A solution of N-methyl-N-(4-tolyl)methanesulphonamide (0.31 g, 1.54 mmol), N-bromosuccinimide (0.28 g, 1.55 mmol) and 2,2'-azobisisobutyronitrile (20 mg) in carbon tetrachloride (20 ml) was refluxed for 2 hours. The mixture was then cooled to ambient temperature and filtered. The solvent was evaporated and the residue partitioned between ethyl acetate (50 ml) and water (50 ml), washed with brine (50 ml) and dried (MgSO$_4$). The solvent was evaporated yielding N-(4-bromomethylphenyl)-N-methylmethanesulphonamide (0.24 g, 54%) which was used without further purification.

EXAMPLE 2

Using a similar procedure to that described in Example 1, except that N-(4-bromomethyl-2-chlorophenyl)-N-methylmethanesulphonamide was used in place of N-(4-bromomethylphenyl)-N-methylmethanesulphonamide, there was obtained N-(2-chloro-4-[5-fluoro -3-(4-methoxytetrahydropyran-4-yl)phenoxymethyl]-phenyl}-N-methylmethanesulphonamide (0.34 g, 60%), m.p. 126°–128° C. (triturated with ether).

The N-(4-bromomethyl-2-chlorophenyl)-N-methylmethanesulphonamide used as starting material was obtained as follows:

A solution of 2-chloro-4-methylaniline (5.00 g) and triethylamine (3.57 g) in dichloromethane (100 ml) was cooled to 0° C. Methanesulphonyl chloride (4.04 g) was added dropwise and the mixture stirred at ambient temperature overnight. The mixture was then washed with 2N aqueous hydrochloric acid solution (50 ml) and the solvent removed by evaporation. The residue was dissolved in ethyl acetate (75 ml) extracted with 2N aqueous sodium hydroxide solution (2×50 ml). The aqueous phase was acidified with 2N aqueous hydrochloric acid solution and extracted with ethyl acetate (2×75 ml). This was subsequently dried (MgSO$_4$) and the solvent evaporated. Thus was obtained N-(2-chloro-4-methylphenyl)methanesulphonamide (2.5 g, 32%). NMR Spectrum 2.33 (3H, s), 2.97 (3H, s), 6.6 (1H, s), 7.10 (1H, d), 7.25 (1H, s), 7.52 (1H, d).

A solution of the product so obtained (1.87 g) in DMF (20 ml) potassium carbonate (3.45 g) and methyl iodide (2.84 g) was stirred at ambient temperature for 18 hours. The mixture was then quenched with water (100 ml) and extracted with ethyl acetate (2×75 ml). The combined organic extracts were then washed with 2N aqueous sodium hydroxide solution (50 ml), brine (50 ml) and dried (MgSO$_4$). The solvent was evaporated to give N-(2-chloro-4-methylphenyl)-N-methylmethanesulphonamide as an oil (1.7 g, 85%). NMR Spectrum 2.35 (3H, s), 3.00 (3H, s), 3.28 (3H, s), 7.10 (1H, m), 7.25 (1H, d), 7.36 (1H, d).

Bromination of N-(2-chloro-4-methylphenyl)-N-methylmethanesulphonamide was carried out using a similar procedure to that described in Example 1, except that N-(2-chloro-4-methylphenyl)-N-methylmethanesulphonamide was used in place of N-methyl-N-(4-tolyl)-methanesulphonamide. There was thus obtained N-(4-bromomethyl-2-chlorophenyl) -N-methylmethanesulphonamide which was used without further purification.

EXAMPLE 3

A solution of N-(4-iodophenyl)-N-methylmethanesulphonamide (0.31 g, 1 mmol), 4-(3-mercaptophenyl)-4-methoxytetrahydropyran (0.22 g), potassium carbonate (20 mg) and copper (I) chloride (30 mg) in DMF (20 ml) was heated to 140° C. and stirred for 3 hours. Ethyl acetate (40 ml) and water (40 ml) were added and the mixture was filtered through celite. The filtrate was washed with water (40 ml) and brine (40 ml), dried (MgSO$_4$) and the solvent evaporated. The product was purified by column chromatography, thus N-{4-[3-(4-methoxytetrahydropyran-4-yl)phenylthio]-phenyl}-N-methylmethanesulphonamide was obtained as an oil (0.12 g, 42%). NMR Spectrum 1.85–2.10 (4H, m), 2.85 (3H, s) 3.00 (3H, s), 3.30 (3H, s), 3.75–3.90 (4H, m), 7.25–7.35 (8H, m).

The 4-(3-mercaptophenyl)-4-methoxytetrahydropyran used as starting material was obtained as follows:-

A solution of 1,3-dibromobenzene (23.8 g) in THF (120 ml) was cooled to −78° C. under an atmosphere of argon and n-butyl lithium (1.6 M in hexane, 62.5 ml) was added dropwise. The mixture was stirred at −78° C. for 30 minutes and a solution of tetrahydropyran-4-one (10 g) in THF (40 ml) was added. The resultant suspension was stirred at −78° C. for 1 hour, allowed to warm to ambient temperature and then stirred for 30 minutes. The mixture was poured into brine (250 ml) and extracted with diethyl ether. The organic phase was dried (MgSO$_4$) and evaporated. The residue was triturated under hexane and the resultant solid (16.8 g) was filtered off.

A solution of the product so obtained in DMF (100 ml) was added dropwise to a slurry of sodium hydride (60% w/w dispersion in mineral oil; 5.25 g) in DMF (10 ml) and the mixture was stirred at ambient temperature for 90 minutes. Methyl iodide (36.5 g) was added and the mixture was stirred at ambient temperature for 16 hours. Ethanol (2 ml) and water (500 ml) were added in turn and the mixture was extracted with diethyl ether (3×200 ml). The combined extracts were washed with water, dried (MgSO₄) and evaporated. The residue was purified by column chromatography using increasingly polar mixtures of hexane and ethyl acetate as eluent. There was thus obtained 4-(3-bromophenyl)-4-methoxytetrahydropyran (12 g, 44%) as a solid. NMR Spectrum (CDCl₃, δ values) 1.88–2.1 (m, 4H), 3.0 (s, 3H), 3.78–3.95 (m, 4H), 7.2–7.35 (m, 2H), 7.42 (m, 1H), 7.55 (m, 1H).

A solution of a portion (1 g) of the product so obtained in THF (4 ml) was cooled to −80° C. under an atmosphere of argon and n-butyl lithium (1.6 M in hexane, 2.4 ml) was added dropwise. The mixture was stirred at −80° C. for 30 minutes, sulphur (0.12 g) was added and the mixture was stirred at -80° C. for a further 30 minutes. Water (10 ml) was added and the mixture was allowed to warm to ambient temperature. The mixture was extracted with diethyl ether (10 ml). The aqueous phase was acidified to pH4 by the addition of dilute aqueous hydrochloric acid solution and extracted with diethyl ether (2×10 ml). The combined organic extracts were dried (MgSO₄ and evaporated. There was thus obtained the required starting material as an oil (0.5 g) which crystallised on standing and was used without further purification.

The N-(4-iodophenyl)-N-methylmethanesulphonamide used as starting material was obtained as follows:-

A solution of 4-iodoaniline (3.50 g, 16 mmol) and pyridine (12.64 g) in dichloromethane (120 ml) was stirred at ambient temperature. Methanesulphonyl chloride (1.83 g, 16 mmol) was added dropwise and the whole mixture was stirred for 18 hours. The solvent was evaporated and the residue partitioned between ethyl acetate (120 ml) and water (120 ml). The organic phase was washed with 2N aqueous sulphuric acid solution (2×75 ml), dried (MgSO₄) and the solvent evaporated. Thus was obtained N-(4-iodophenyl)methanesulphonamide (2.04 g, 43%), m.p. 131°–133° C. (recrystallised from ethyl acetate/hexane).

A solution of the product so obtained (0.89 g, 3 mmol) in acetaone (50 ml) with potassium carbonate (1.38 g) and methyl iodide (0.71 g, 5 mmol) was stirred at ambient temperature for 20 hours. Ethyl acetate (100 ml) was added to the mixture which was then washed with brine (50 ml), dried (MgSO₄) and the solvent evaporated. Thus was obtained N-(4-iodophenyl)-N-methylmethanesulphonamide (0.56 g, 60%), m.p. 103°–104° C. (recrystallised from ethyl acetate/hexane).

EXAMPLE 4

Using a similar procedure to that described in Example 3, except that the appropriate N-(4-iodophenyl)sulphonamide was used in place of N-(4-iodophenyl)-N-methylmethanesulphonamide, there were obtained the compounds described in the following table:

TABLE 1

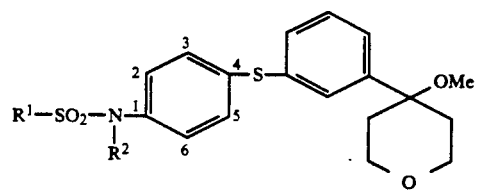

| Ex 4 Compd. No. | N-Phenyl substituent | R¹ | R² | Yield (%) | m.p. |
|---|---|---|---|---|---|
| 1ᵃ | 3-chloro | methyl | methyl | 76 | oil |
| 2ᵇ | no substituent | methyl | H | 68 | oil |
| 3ᶜ | no substituent | methyl | ethyl | 82 | gum |
| 4ᵈ | no substituent | ethyl | methyl | 82 | gum |
| 5ᵉ | 3-methyl | methyl | methyl | 35 | gum |
| 6ᶠ | 2-chloro | methyl | methyl | 48 | gum |
| 7ᵍ | no substituent | methyl | allyl | 31 | gum |
| 8ʰ | no substituent | methyl | benzyl | 35 | gum |
| 9ⁱ | no substituent | phenyl | methyl | 30 | gum |

NOTES a. The product gave the following characteristic NMR signals: 1.90–2.10 (4H, m), 2.85 (3H, s), 3.0 (3H, s), 3.30 (3H, s), 3.75–3.90 (4H, m), 6.90 (1H, d), 7.15 (1H, m), 7.35–7.45 (4H, m), 7.50 (1H, d).

The N-(3-chloro-4-iodophenyl)-N-methylmethanesulphonamide used as a starting material was obtained using the procedures described in Example 3 for the preparation of N-(4-iodophenyl)-N-methylmethanesulphonamide except that 3-chloro-4-iodoaniline was used in place of 4-iodoaniline.

b. The product gave the following characteristic NMR signals:-1.85–2.05 (4H, m), 2.95 (3H, s), 3.05 (3H, s), 3.75–3.90 (4H, m), 6.65 (1H, s), 7.15–7.40 (8H, m).

The N-(4-iodophenyl)methanesulphonamide used as starting material was obtained as described in Example 3.

c. The product gave the following characteristic NMR signals:-1.15 (3H, t), 1.85–2.0 (4H, m), 2.85 (3H, s), 3.0 (3H, s), 3.70 (2H, q), 3.70–3.90 (4H, m), 7.30–7.45 (8H, m).

The N-(4-iodophenyl)-N-ethylmethanesulphonamide used as starting material was obtained as described in Example 3 for the preparation of N-(4-iodophenyl)-N-methylmethanesulphonamide except that ethyl iodide was used in place of methyl iodide.

d. The product gave the following characteristic NMR signals:-1.20 (3H, t), 1.80–1.95 (4H, m), 2.85 (3H, s), 3.15 (2H, q), 3.25 (3H, s), 3.55–3.75 (4H, m), 7.25–7.45 (8H, m).

The N-(4-iodophenyl)-N-methylethanesulphonamide used as starting material was obtained as follows:-

To a solution of N-methylaniline (14.9 g) and triethylamine (15.1 g) in dichloromethane (250 ml) at 0° C. was added acetyl chloride (11.0 g) dropwise. The mixture was stirred at ambient temperature for 1 hour, then washed with 2N aqueous hydrochloric acid solution (75 ml), dried (MgSO₄) and the solvent evaporated. Thus was obtained N-methylacetanilide (15.6 g, 75%), m.p. 95°–97° C. (recrystallised from ethyl acetate/hexane).

The product so obtained (5.96 g), iodine (5.08 g) and iodic acid (2.29 g) were heated in glacial acetic acid (30 ml) and concentrated sulphuric acid (4 ml) at 85° C. for 3.5 hours. The mixture was then cooled to ambient temperature and ethyl acetate (125 ml) and water (75 ml) were added. Solid sodium bicarbonate was added to neutralise the mixture which was then washed with water (75 ml) and brine (75 ml). After drying (MgSO$_4$) the solvent was evaporated to leave 4'-iodo-N-methylacetanilide (7.04, 64%), m.p. 140°–141° C. (recrystallised from ethyl acetate/hexane).

A solution of the product so obtained (6.05 g) in 2N aqueous sodium hydroxide solution (30 ml) and ethanol (30 ml) was refluxed for 8 hours. The solvent was evaporated and the residue partitioned between ethyl acetate (110 ml) and water (100 ml). The organic phase was washed with brine (75 ml), dried (MgSO$_4$) and the solvent evaporated to give 4-iodo-N-methylaniline as an oil (4.97 g, 97%). NMR Spectrum 2.80 (3H, s), 6.40 (2H, d), 7.45 (2H, d).

The product so obtained was used in place of 4-iodoaniline in the procedure described in Example 3 for the preparation of N-(4-iodophenyl) methanesulphonamide and ethanesulphonyl chloride was used in place of methanesulphonyl chloride. Thus was obtained N-(4-iodophenyl)-N-methylethanesulphonamide as an oil. NMR Spectrum 1.45 (3H, t), 3.00 (2H, q), 3.35 (3H, s), 7.15 (2H, m), 7.70 (2H, m).

e. The product gave the following characteristic NMR signals:-1.85–2.05 (4H, m), 2.38 (3H, s), 2.85 (3H, s), 2.96 (3H, s), 3.30 (3H, s), 3.75–3.90 (4H, m), 7.05–7.35 (7H, m).

The N-(4-iodo-3-methylphenyl)-N-methylmethanesulphonamide used as starting material was obtained as follows:-

N-Methyl-N-(3-tolyl)methanesulphonamide was prepared as for the preparation of N-(4-iodophenyl)-N-methylmethanesulphonamide described in Example 3, except that 3-methylaniline was used in place of 4-iodoaniline.

A solution of N-methyl-N-(3-tolyl)methanesulphonamide (0.12 g), iodine (76 g) and iodic acid (35 mg) in glacial acetic acid (5 ml) and concentrated sulphuric acid (0.6 ml) was stirred at 80° C. for 2.5 hours. Ethyl acetate (40 ml) and water (40 ml) were then added and the mixture neutralised with solid sodium bicarbonate. The organic phase was washed with brine (30 ml), dried (MgSO$_4$) and the solvent evaporated to leave N-(4-iodo-3-methylphenyl)-N-methylmethanesulphonamide (0.22 g, 90%), m.p. 85°–87° C.

f. The product gave the following characteristic NMR signals:-1.90–2.10 (4H, m), 2.98 (3H, s), 3.02 (3H, s), 3.28 (3H, s), 3.75–3.90 (4H, m), 7.05–7.55 (7H, m).

The N-(2-chloro-4-iodophenyl)-N-methylmethanesulphonamide used as a starting material was obtained using the procedures described in Example 3 for the preparation of N-(4-iodophenyl)-N-methylmethanesulphonamide except that 2-chloro-4-iodoaniline was used in place of 4-iodoaniline.

g. The product gave the following characteristic NMR signals:-1.90–2.10 (4H, m), 2.90 (3H, s), 3.0 (3H, s), 3.70–3.90 (4H, m), 4.24 (2H, d), 5.15 (1H, d), 5.25 (1H, d), 5.70–5.95 (1H, m), 7.1–7.6 (8H, m).

The N-allyl-N-(4-iodophenyl)methanesulphonamide used as a starting material was obtained using the procedures described in Example 3 for the preparation of N-(4-iodophenyl)-N-methylmethanesulphonamide, except that allyl bromide was used in place of methyl iodide.

h. The product gave the following characteristic NMR signals:-1.85–2.05 (4H, m), 2.95 (6H, s), 3.75–3.90 (4H, m), 4.82 (2H, s), 7.10–7.45 (13H, m).

The N-benzyl-N-(4-iodophenyl)methanesulphonamide used as a starting material was obtained using the procedures described in Example 3 for the preparation of N-(4-iodophenyl)-N-methylmethanesulphonamide, except that benzyl bromide was used in place of methyl iodide.

i. The product gave the following characteristic NMR signals:-1.85–2.05 (4H, m), 2.97 (3H, s), 3.18 (3H, s), 3.75–3.90 (4H, m), 7.0–7.60 (13H, m).

The N-(4-iodophenyl)-N-methylbenzenesulphonamide used as a starting material was obtained using the procedures described in Example 3 for the preparation of N-(4-iodophenyl-N-methylmethanesulphonamide, except that benzenesulphonyl chloride was used in place of methanesulphonyl chloride.

EXAMPLE 5

A solution of 5-iodo-N-mesylindoline (0.32 g, 1 mmol), 4-(3-mercaptophenyl)-4-methoxytetrahydropyran (0.23 g, 1 mmol), copper (I) chloride (30 mg) and potassium carbonate (0.28 g) in DMF (10 ml) was heated at 140° C. for 5 hours. After cooling ethyl acetate (75 ml) and water (75 ml) were added and the mixture was filtered through celite. The filtrate was washed with brine (50 ml), dried (MgSO$_4$) and the solvent evaporated. The crude product was purified by column chromatography to give 5-[3-(4-methoxytetrahydropyran-4-yl)phenylthio]-N-mesylindoline (0.23 g, 55%), m.p. 114°–118° C. (recrystallised from ethyl acetate/hexane).

NMR Spectrum 1.80–2.08 (4H, m), 2.90 (3H, s), 2.95 (3H, s), 3.12 (2H, t), 3.72–3.90 (4H, m), 4.00 (2H, t), 7.10–7.40 (7H, m).

The 5-iodo-N-mesylindoline used as starting material was prepared as follows:-

N-mesylindoline was obtained using the procedures described in Example 3 for the preparation of N-(4-iodophenyl)methanesulphonamide, except that indoline was used in place of 4-iodoaniline. The N-mesylindoline so obtained (0.67 g, 5 mmol), iodine (0.64 g) and iodic acid (0.29 g) in glacial acetic acid (4 ml) and concentrated sulphuric acid (0.5 ml) were heated to 85° C. for 2 hours. The mixture was diluted with water (75 ml) and ethyl acetate (75 ml) and neutralised with solid sodium bicarbonate. The organic phase was washed with brine (50 ml), dried (MgSO$_4$) treated with charcoal (1 g), filtered and the solvent evaporated. Polar material was removed by filtration through silica and the 5-iodo-N-mesylindoline thus obtained was used without further purification.

EXAMPLE 6

Using a similar procedure to that described in Example 5, except that the appropriate iodosulphonamide was used in place of 5-iodo-N-mesylindoline, there were obtained the compounds described in the following table:

TABLE II

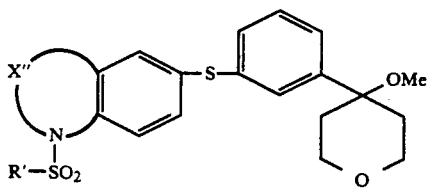

| Ex 6 Compd. No. | X'' | R' | m.p. |
|---|---|---|---|
| 1[a] | —CH₂CH₂CH₂— | methyl | gum |
| 2[b] | —CH₂CH₂— | ethyl | gum |

NOTES a. The product gave the following characteristic NMR signals: 1.85-2.10 (6H, m), 2.80 (2H, t), 2.92 (3H, s), (3.75-3.90 (6H, m), 7.10-7.65 (7H, m).

The 6-iodo-N-mesyl-1,2,3,4-tetrahydroquinoline used as starting material was obtained using the procedures described in Example 5 for the preparation of 5-iodo-N-mesylindoline except that 1,2,3,4-tetrahydroquinoline was used in place of indoline.

b. The product gave the following characteristic NMR signals:-1.38 (3H, t), 1.82-2.05 (4H, m), 2.96 (3H, s), 3.05-3.20 (4H, m), 3.75-3.90 (4H, m), 4.10 (2H, m), 7.10-7.35 (7H, m).

The 5-iodo-N-ethylsulphonylindoline used as starting material was obtained using the procedures described in Example 5 for the preparation of 5-iodo-N-mesylindoline, except that ethanesulphonyl chloride was used in place of methanesulphonyl chloride.

EXAMPLE 7

Sodium hydride (79 mg, 50% dispersion in mineral oil, 1.65 mmol) was added to a solution of N-(6-chloropyrid-3-yl)-N-methyl-methanesulphonamide (0.33 g) and 4-(3-mercaptophenyl)-4-methoxytetrahydropyran (0.34 g) in DMF (10 ml). The mixture was stirred at ambient temperature for 15 minutes and heated at 140° C. for 1.5 hours. After cooling, it was partitioned between water (75 ml) and ethyl acetate (75 ml). The organic phase was washed with brine (50 ml), dried (MgSO₄) and the solvent evaporated. The product was purified by column chromatography to give N-(6-[3-(4-methoxytetrahydropyran-4-yl)phenylthio]pyrid-3-yl}-N-methylmethanesulphonamide as a gum (0.25 g, 41%).

NMR Spectrum 1.85-2.10 (4H, m), 2.85 (3H, s), 3.0 (3H, s), 3.30 (3H, s), 3.75-3.90 (3H, s), 6.90 (1H, d), 7.45-7.65 (5H, m), 8.40 (1H, d).

The N-(6-Chloropyrid-3-yl)-N-methylmethanesulphonamide used as starting material was prepared as follows:-

N-(2-chloropyrid-5-yl)methanesulphonamide was obtained using the procedure described for the preparation of N-(4-iodophenyl)methanesulphonamide, except that 5-amino-2-chloropyridine was used in place of 4-iodoaniline.

Sodium hydride (0.12 g, 50% dispersion in mineral oil, 2.5 mmol) was added to a solution of the product so obtained (0.50 g) in DMF (10 ml). The mixture was stirred at ambient temperature for 15 minutes. Methyl iodide (0.36 g) was added and the mixture stirred at ambient temperature for a further 1 hour. The mixture was partitioned between water (75 ml) and ethyl acetate (75 ml), the organic phase washed with water (50 ml) and brine (50 ml), dried (MgSO₄ and the solvent evaporated to leave N-(6-chloropyrid-3-yl)-N-methylmethanesulphonamide (0.40 g, 75%), m.p. 87°-90° C.

EXAMPLE 8

Using a similar procedure to that described in Example 3, except that the appropriate N-(4-iodophenyl)sulphonamide was used in place of N-(4-iodophenyl)-N-methylmethanesulphonamide, there were obtained the compounds described in the following table:-

TABLE III

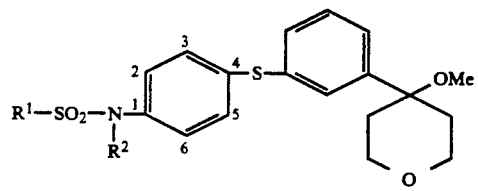

| Ex. 8 Compd. No. | N-Phenyl Substituent | R¹ | R² | Yield (%) | m.p. (°C.) |
|---|---|---|---|---|---|
| 1[a] | 2-chloro | methyl | H | 50 | 101-102 |
| 2[b] | no substituent | phenyl | H | 37 | gum |

NOTES a. The product was recrystallised from a mixture of hexane and ethyl acetate. N-(4-Iodophenyl)methanesulphonamide is described in the portion of Example 3 which is concerned with the preparation of starting materials.

b. The product gave the following characteristic NMR signals:-1.85-2.05 (4H, m), 2.93 (3H, s), 3.75-3.90 (4H, m), 6.95-7.8 (13H, m).

The N-(4-iodophenyl)benzenesulphonamide used as a starting material was obtained by the reaction of benzenesulphonyl chloride and 4-iodoaniline using a similar procedure to that described in the portion of Example 3 which is concerned with the preparation of N-(4-iodophenyl)methanesulphonamide.

EXAMPLE 9

Using a similar procedure to that described in Example 3, except that the appropriate N-(4-iodophenyl)sulphonamide was used in place of N-(4-iodophenyl)-N-methylmethanesulphonamide and that 4-(5-fluoro-3-mercaptophenyl)-4-methoxytetrahydropyran was used in place of 4-(3-mercaptophenyl)-4-methoxytetrahydropyran, there were obtained the compounds described in the following table:-

TABLE IV

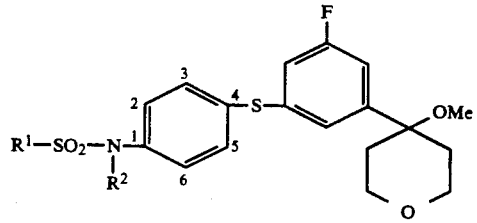

| Ex. 9 Compd. No. | N-Phenyl Substituent | R¹ | R² | Yield (%) | m.p. (°C.) |
|---|---|---|---|---|---|
| 1[a] | no substituent | methyl | methyl | 67 | 108-111 |
| 2[a] | 3-chloro | methyl | methyl | 60 | 113-115 |

TABLE IV-continued

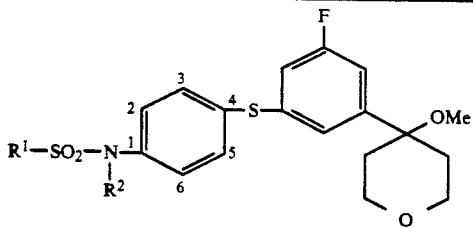

| Ex. 9 Compd. No. | N-Phenyl Substituent | R¹ | R² | Yield (%) | m.p. (°C.) |
|---|---|---|---|---|---|
| 3[b] | 2-chloro | methyl | H | 73 | gum |
| 4[c] | 3-chloro | methyl | H | 44 | gum |
| 5[d] | 2-fluoro | methyl | H | 58 | 101–102 |

NOTES

The 4-(5-fluoro-3-mercaptophenyl)-4-methoxytetrahydropyran used as a starting material for each of the compounds described in Table IV was obtained as follows:-

Benzyl mercaptan (0.94 ml) was added dropwise to a mixture of sodium hydride (60% w/w dispersion in mineral oil; 0.35 g) and DMF (5 ml) which was cooled in a water bath. The mixture was stirred at ambient temperature for 30 minutes. The mixture so obtained was added dropwise to a mixture of 1-bromo-3,5-difluorobenzene (2.78 ml) and DMF (5 ml) which was cooled in an ice bath to 5° C. The resultant mixture was stirred at ambient temperature for 1 hour. The mixture was partitioned between diethyl ether and water. The organic phase was washed with water, dried (MgSO₄) and evaporated. There was thus obtained benzyl 3-bromo-5-fluorophenyl sulphide (2.5 g). NMR Spectrum (CDCl₃, δ values) 4.13 (s, 2H), 6.90 (m, 1H), 7.04 (m, 1H), 7.2–7.35 (m, 6H).

A Grignard reagent was prepared by heating a mixture of 1,2-dibromoethane (10 drops), magnesium (0.24 g) and THF (25 ml) to 60° C. for 5 minutes, by adding benzyl 3-bromo-5-fluorophenyl sulphide (2.5 g) and by heating the resultant mixture to 60° C. for 30 minutes. The reagent was cooled in an ice bath, tetrahydropyran-4-one (0.8 ml) was added and the mixture was stirred for 30 minutes and then allowed to warm to ambient temperature. A saturated aqueous ammonium chloride solution (30 ml) was added and the mixture was partitioned between diethyl ether and water. The organic phase was washed with water and with brine, dried (MgSO₄) and evaporated. The residue was purified by column chromatography using initially hexane and then increasingly polar mixtures of hexane and ethyl acetate as eluent. There was thus obtained 4-(3-benzylthio-5-fluorophenyl)-4-hydroxytetrahydropyran (1.02 g).

Sodium hydride (60% w/w dispersion in mineral oil; 0.2 g) was added portionwise to a mixture of the product so obtained and DMF (5 ml) and the mixture was stirred at ambient temperature for 1 hour. Methyl iodide (0.6 ml) was added and the mixture was stirred at ambient temperature for 1 hour. The mixture was partitioned between diethyl ether and water. The organic phase was dried (MgSO₄) and evaporated. There was thus obtained 4-(3-benzylthio-5-fluorophenyl)-4-methoxytetrahydropyran (0.8 g) as an oil. NMR Spectrum (CDCl₃, δ values) 1.85 (m, 4H), 2.91 (s, 3H), 3.78 (m, 4H), 4.12 (s, 2H), 6.85–7.05 (m, 3H), 7.25 (m, 5H).

3-Chloroperbenzoic acid (55% w/w technical grade; 0.38 g) was added portionwise to a mixture of a portion (0.4 g) of the product so obtained and chloroform (4 ml) which was cooled in an ice bath to 0° C. The mixture was stirred at 0° C. for 30 minutes and then allowed to warm to ambient temperature. Calcium hydroxide (0.13 g) was added and the mixture was stirred at ambient temperature for 15 minutes. The mixture was filtered and the filtrate was evaporated. Trifluoroacetic anhydride (3 ml) was added to the residue so obtained and the mixture was heated to reflux for 30 minutes. The mixture was evaporated. Methanol (10 ml) and triethylamine (10 ml) were added to the residue and the resultant mixture was evaporated. There was thus obtained 4-(5-fluoro-3-mercaptophenyl)-4-methoxytetrahydropyran (0.37 g) as a gum which was used as the required starting material without further purification.

a. The product was recrystallised from a mixture of hexane and ethyl acetate.

b. The product gave the following characteristic NMR signals: 1.85–2.05 (4H, m), 3.0 (3H, s), 3.05 (3H, s), 3.75 (4H, m), 6.85–7.22 (4H, m), 7.43 (1H, d), 7.63 (1H, d).

The N-(2-chloro-4-iodophenyl)methanesulphonamide used as a starting material was obtained by the reaction of 2-chloro-4-iodoaniline and methanesulphonyl chloride using a similar procedure to that described in the portion of Example 3 which is concerned with the preparation of N-(4-iodophenyl)methanesulphonamide.

c. The product gave the following characteristic NMR signals:- 1.85–2.05 (4H, m), 2.98 (3H, s), 3.08 (3H, s), 3.75–3.9 (4H, m), 6.85–7.38 (6H, The N-(3-chloro-4-iodophenyl)methanesulphonamide used as a starting material was obtained by the reaction of 3-chloro-4-iodoaniline and methanesulphonyl chloride using a similar procedure to that described in the portion of Example 3 which is concerned with the preparation of N-(4-iodophenyl)methansulphonamide.

d. The product was recrystallised from a mixture of hexane and ethyl acetate.

The N-(2-fluoro-4-iodophenyl)methanesulphonamide, m.p. 117°–119° C., used as a starting material was obtained in 70% yield by the reactions of 2-fluoro-4-iodoaniline and methanesulphonyl chloride using a similar procedure to that described in the portion of Example 3 which is concerned with the preparation of N-(4-iodophenyl)-methanesulphonamide.

EXAMPLE 10

Using a similar procedure to that described in Example 3, except that the appropriate N-(4-iodophenyl)sulphonamide was used in place of N-(4-iodophenyl)-N-methylmethanesulphonamide and that 4-(5-fluoro-3-mercaptophenyl)-4-methoxytetrahydropyran, there were obtained the compounds described in the following table:

TABLE V

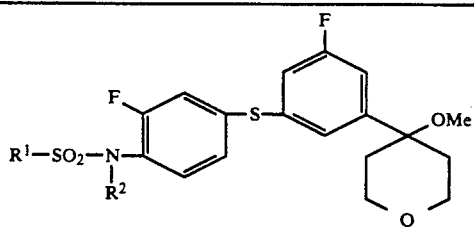

| Ex. 10 Compd. No. | R¹ | R² | Yield (%) | m.p. (°C.) |
|---|---|---|---|---|
| 1[a] | ethyl | H | 45 | 78-81 |
| 2[b] | phenyl | H | 45 | gum |
| 3[c] | 2-methoxycarbonylphenyl | H | 44 | 92-94 |
| 4[d] | 1-naphthyl | H | 68 | 138-139 |
| 5[e] | 8-quinolyl | H | 15 | gum |
| 6[f] | 8-quinolyl | methyl | 35 | gum |

NOTES a. The product was recrystallised from a mixture of hexane and ethyl acetate.

The N-(2-fluoro-4-iodophenyl)ethanesulphonamide used as a starting material was obtained by the reaction of 2-fluoro-4-iodoaniline and ethanesulphonyl chloride using a similar procedure to that described in the portion of Example 3 which is concerned with the preparation of N-(4-iodophenyl)methanesulphonamide. There was thus obtained the required starting material in 77% yield, m.p. 66°-68° C.

b. The product gave the following characteristic NMR signals: 1.82-2.05 (m, 4H), 2.96 (s, 3H), 3.76-3.88 (m, 4H), 6.8 (m, 2H), 6.97 (m, 2H), 7.12 (m, 2H), 7.41-7.62 (m, 4H), 7.8 (m, 2H).

The N-(2-fluoro-4-iodophenyl)benzenesulphonamide used as a starting material was obtained by the reaction of 2-fluoro-4-iodoaniline and benzenesulphonyl chloride using a conventional procedure as described in Example 3. There was thus obtained the required starting material in 50% yield, m.p. 150°-152° C.

c. The product was recrystallised from a mixture of hexane and ethyl acetate.

The N-(2-fluoro-4-iodophenyl)-2-methoxycarbonylbenzene-sulphonamide used as a starting material was obtained by the reaction of 2-fluoro-4-iodoaniline and 2-methoxycarbonylbenzenesulphonyl chloride using a conventional procedure as described in Example 3. There was thus obtained the required starting material in 58% yield, m.p. 103°-104° C.

d. The product was recrystallised from a mixture of hexane and ethyl acetate.

The N-(2-fluoro-4-iodophenyl)-1-naphthalenesulphonamide used as a starting material was obtained by the reaction of 2-fluoro-4-iodoaniline and 1-naphthalenesulphonyl chloride using a conventional procedure as described in Example 3. There was thus obtained the required starting material in 44% yield, m.p. 130°-132° C.

e. The product gave the following characteristic NMR signals: 1.74-2.02 (m, 4H), 2.92 (s, 3H), 3.70-3.90 (m, 4H), 6.70 (m, 1H), 6.82 (m, 1H), 6.92 (m, 1H), 7.04 (m, 2H), 7.52-7.73 (m, 3H), 8.06 (m, 1H), 8.30 (m, 1H), 8.38 (m, 1H), 9.11 (m, 1H).

The N-(2-fluoro-4-iodophenyl)-8-quinolinesulphonamide used as a starting material was obtained by the reaction of 2-fluoro-4-iodoaniline and 8-quinolinesulphonyl chloride using a conventional procedure as described in Example 3. There was thus obtained the required starting material in 39% yield, m.p. 154°-156° C.

f. The product gave the following characteristic NMR signals: 1.83-2.02 (m, 4H), 2.97 (s, 3H), 3.54 (s, 3H), 3.73-3.90 (m, 4H), 6.83 (m, 1H), 6.91-7.08 (m, 3H), 7.18 (m, 1H), 7.30 (m, 1H), 7.51 (m, 2H), 8.03 (m, 1H), 8.23 (m, 1H), 8.37 (m, 1H), 8.98 (m, 1H).

The N-(2-fluoro-4-iodophenyl)-N-methyl-8-quinoline-sulphonamide used as a starting material was obtained by the reaction of N-(2-fluoro-4-iodophenyl)-8-quinolinesulphonamide and methyl iodide using a conventional procedure as described in the last paragraph of Example 3. There was thus obtained the required starting material in 55% yield, m.p. 90°-93° C.

CHEMICAL FORMULAE

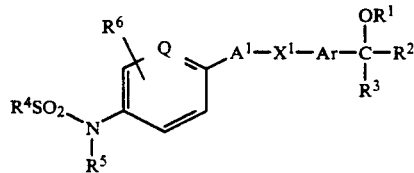

I

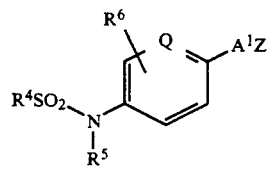

II

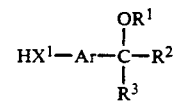

III

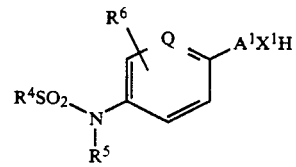

IV

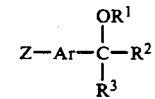

V

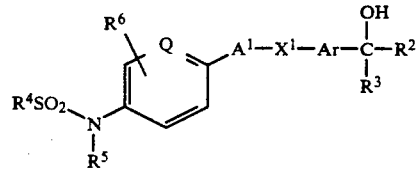

VI

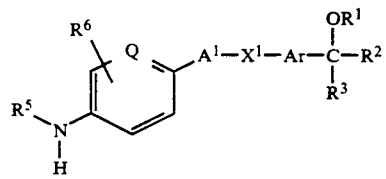

VII

-continued
CHEMICAL FORMULAE
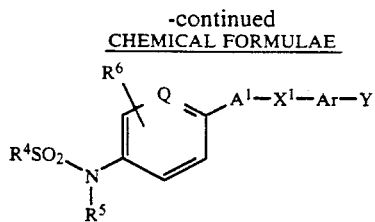
-continued
SCHEME II
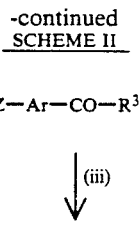
SCHEME I
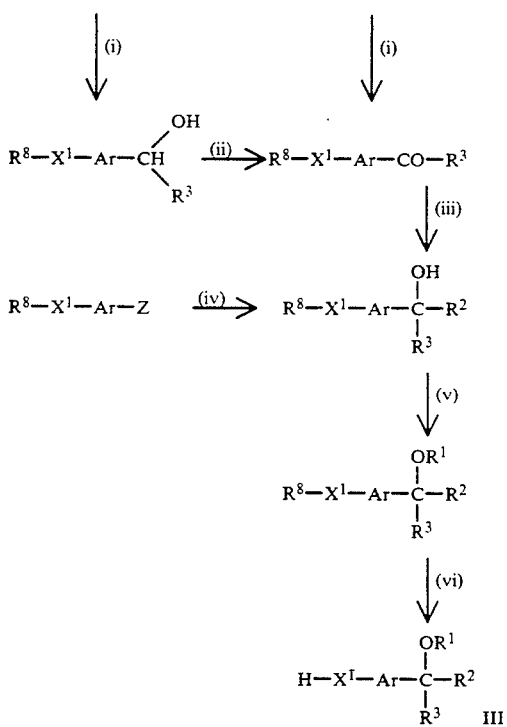
Reagents
(i) $R^3Li$ or $R^3MgZ$, THF;   (ii) DDQ or $MnO_2$;
(iii) $R^2Li$ or $R^2MgZ$, THF; (iv) BuLi or Mg, THF; $R^2COR^3$, THF;
(v) $R^1Z$, base;               (vi) Conventional removal of the
protecting group $R^8$ which is, e.g., COMe, THP, $CH_2Ph$ or Me.
SCHEME II
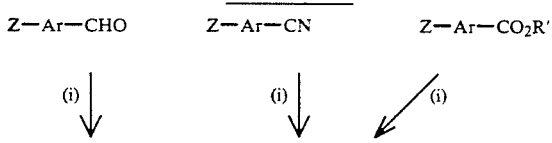
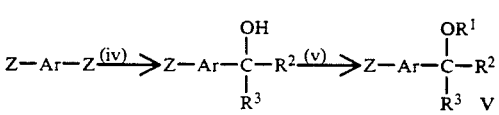
Reagents
(i) to (v) as in Scheme I
Note R' = (1-4C)alkyl such as Me or Et

SCHEME III

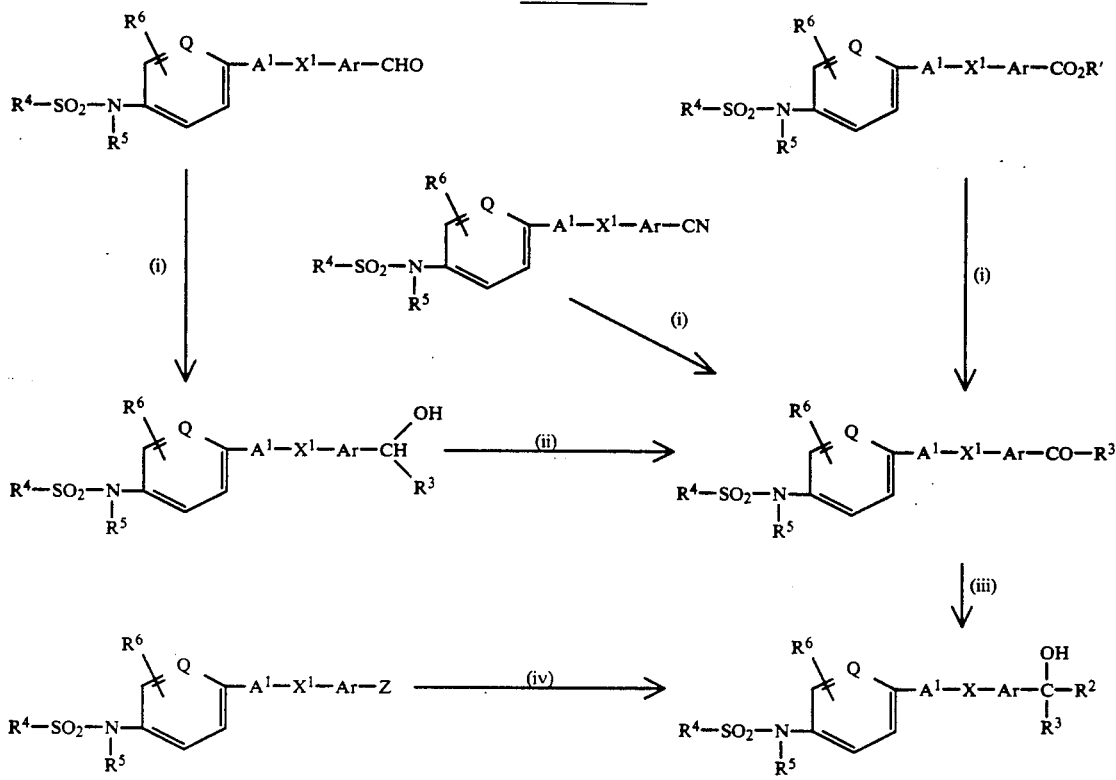

Reagents:
- (i) to (iv) as in Scheme I

What is claimed is:
1. A sulphonamide derivatives of the formula I

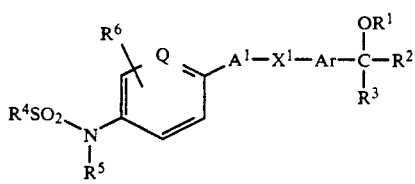

wherein $R^1$ is (1-4C)alkyl, (3-4C)alkenyl or (3-4C)alkynyl; and wherein $R^2$ and $R^3$ together form a group of the formula $-A^2-X^2-A^3-$ which, together with the carbon atom to which $A^2$ and $A^3$ are attached, defines a ring having 6 ring atoms, wherein $A^2$ and $A^3$, which may be the same or different, each is (1-3C)alkylene and $X^2$ is oxy, and which ring may bear one, two or three substituents, which may be the same or different, selected from hydroxy, 1-4C)alkyl and (1-4C)alkoxy; wherein $A^1$ is a direct link to $X^1$ or is (1-3C)alkylene; wherein $X^1$ is oxy, thio, sulphinyl, sulphonyl or imino; wherein Ar is phenylene which may optionally bear one or two substituents selected from halogeno, hydroxy, amino, nitro, cyano, carbamoyl, ureido, (1-4C)alkyl, (1-4C)alkoxy, (1-4C)alkylamino, di-[(1-4C)alkyl]amino, fluoro-(1-4C)alkyl and (2-4C)alkanoylamino;
and wherein Q is of the formula $CR^7$, wherein $R^7$ is hydrogen, halogeno, (1-4C)alkyl, (1-4C)alkoxy, hydroxy, amino, nitro, cyano, carbamoyl, ureido, (1-4C)alkylamino, di-[(1-4C)alkyl]amino, fluoro-(1-4C)alkyl, (2-4C)alkanoylamino or (2-4C)alkenyl; wherein $R^4$ is (1-4C)alkyl, (3-4C)alkenyl or (3-4C)alkynyl or $R^4$ is phenyl, benzyl or pyridyl each of which may optionally bear one or two substituents selected from halogeno, (1-4C)alkoxy, (1-4C)alkyl, hydroxy, cyano, nitro, amino, trifluoromethyl, carbamoyl, ureido, (1-4C)alkylamino, di-[(1-4C)alkyl]amino and (2-4C)alkanoylamino; $R^5$ and $R^6$ are joined to form (2-4C)alkylene or (2-4C)alkenylene either of which may optionally bear one or two substituents selected from (1-4C)alkyl and halogens;
or a pharmaceutically-acceptable salt thereof.

2. A sulphonamide derivative of the formula I as claimed in claim 1 wherein $R^4$ may be phenyl, benzyl, naphthyl or pyridyl each of which may optionally bear one or two substituents selected from halogeno, (1-4C)alkoxy, (1-4C)alkyl, hydroxy, cyano, nitro, amino, trifluoromethyl, carbamoyl, ureido, (1-4C)alkylamino, di-[(1-4C)alkyl]amino, (2-4C)alkanoylamino and (1-4C)alkoxycarbonyl; or a pharmaceutically-acceptable salt thereof.

3. A sulphonamide derivative of the formula I as claimed in claim 1 wherein $R^1$ is methyl; $R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;
$A^1$ is a direct link to $X^1$, or is methylene;

$X^1$ is thio or oxy;

Ar is 1,3-phenylene which may optionally bear a fluoro substituent;

Q is of the formula $CR^7$ wherein $R^7$ is hydrogen, methyl or chloro;

$R^4$ is methyl, ethyl or phenyl; and $R^5$ and $R^6$ are joined to form ethylene or trimethylene; or a pharmaceutically-acceptable salt thereof.

4. A pharmaceutical composition which comprises a sulphonamide derivative of the formula I, or a pharmaceutically-acceptable salt thereof, as claimed in any one of claims 1 to 3 in association with a pharmaceutically-acceptable diluent or carrier.

5. A method of treating a disease or medical condition mediated alone or in part by one or more leukotrienes which comprises administering to a warm-blooded animal requiring such treatment an effective amount of a sulphonamide derivatives of the formula I, or a pharmaceutically-acceptable salt thereof, as claimed in any one of claims 1 to 3.

6. A sulphonamide derivative of the formula I, or a pharmaceutically-acceptable salt thereof, as claimed in claim 1 being 5-[3-(4-methoxytetrahydropyran-4-yl)phenylthio]-N-mesylindoline.

* * * * *